G US006465202B1

(12) United States Patent
Tyrrell

(10) Patent No.: US 6,465,202 B1
(45) Date of Patent: Oct. 15, 2002

(54) METHOD FOR STABILIZING AMINOTRANSFERASE ACTIVITY IN A BIOLOGICAL FLUID

(75) Inventor: Steven P. Tyrrell, Highland Park, IL (US)

(73) Assignee: BioSafe Laboratories, Inc., Chicago, IL (US)

( * ) Notice: Subject to any disclaimer, the term of this patent is extended or adjusted under 35 U.S.C. 154(b) by 0 days.

(21) Appl. No.: 09/506,305

(22) Filed: Feb. 17, 2000

(51) Int. Cl.$^7$ .................................................. C12Q 1/48
(52) U.S. Cl. ............................ 435/15; 435/16; 435/188
(58) Field of Search ................................ 435/6, 15, 16, 435/26, 69.2, 184, 188, 193

(56) References Cited

U.S. PATENT DOCUMENTS

| | | | |
|---|---|---|---|
| 3,640,267 A | 2/1972 | Hurtig et al. .................. | 128/2 |
| 4,990,457 A | 2/1991 | Tanaka et al. | |
| 5,059,525 A | 10/1991 | Bartl et al. | |
| 5,147,803 A | * 9/1992 | Enomoto ..................... | 436/16 |
| 5,244,788 A | 9/1993 | Hubscher | |
| 5,558,834 A | 9/1996 | Chu et al. | |
| 5,788,942 A | 8/1998 | Kitani et al. | |
| 5,807,358 A | 9/1998 | Herweck et al. | |
| 5,824,268 A | 10/1998 | Bernstein et al. ............. | 422/56 |
| 5,834,226 A | * 11/1998 | Maupin ....................... | 435/15 |
| 5,860,929 A | 1/1999 | Rubin et al. | |

FOREIGN PATENT DOCUMENTS

| | | | |
|---|---|---|---|
| PL | PL 146644 | * | 2/1989 |
| WO | WO 79/01131 | | 5/1979 |

OTHER PUBLICATIONS

Gowenlock A. Varleys's Practical Clinical Biochemistry 6th ed., CRC Press, Boca Raton, FL, 1990.*
Breuer Von J. Enzyme Activites in Serum and Plasma . . . Z Klin Chem Klin Biochem 13(8)355–360, 1975.*
Abstract, "The effect of operating and formulation variables on the morphology of spray–dried protein particles.", Maa YF, et al., *Pharm Dev Technol* 1997 Aug.; 2(3):213–23.
Abstract, "Determination of vitamin A in dried human blood spots by high–performance capillary electrophoresis with laser–excited fluorescence detection.", Shi H, et al., *J Chromatogr B Biomed Appl* 1995 Mar. 10; 665(1):89–96.
Abstract, "Characterization of differentiated Syrian golden hamster pancreatic duct cells maintained in extended monolayer culture.", Hubchak S, et al., *In Vitro Cell Dev Biol* 1990 Sep.; 26(9):889–97.

* cited by examiner

*Primary Examiner*—Ralph Gitomer
(74) *Attorney, Agent, or Firm*—Olson & Hierl, Ltd.

(57) ABSTRACT

Methods and compositions for the stabilization of aminotransferase activity of plasma or serum are provided. Such methods will be useful in the accurate determination of tests associated with liver toxicity.

29 Claims, 6 Drawing Sheets

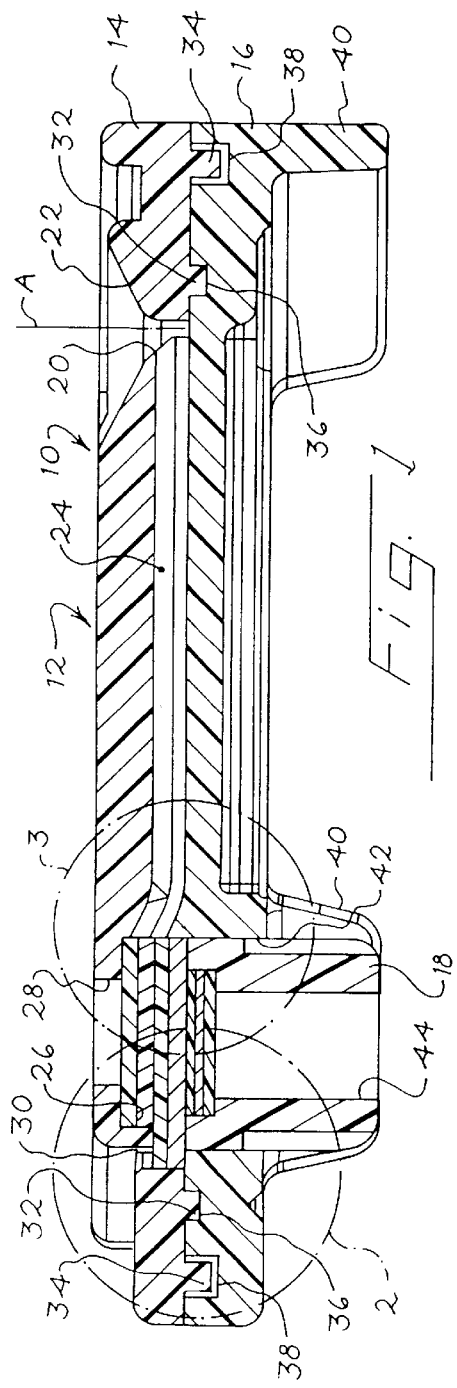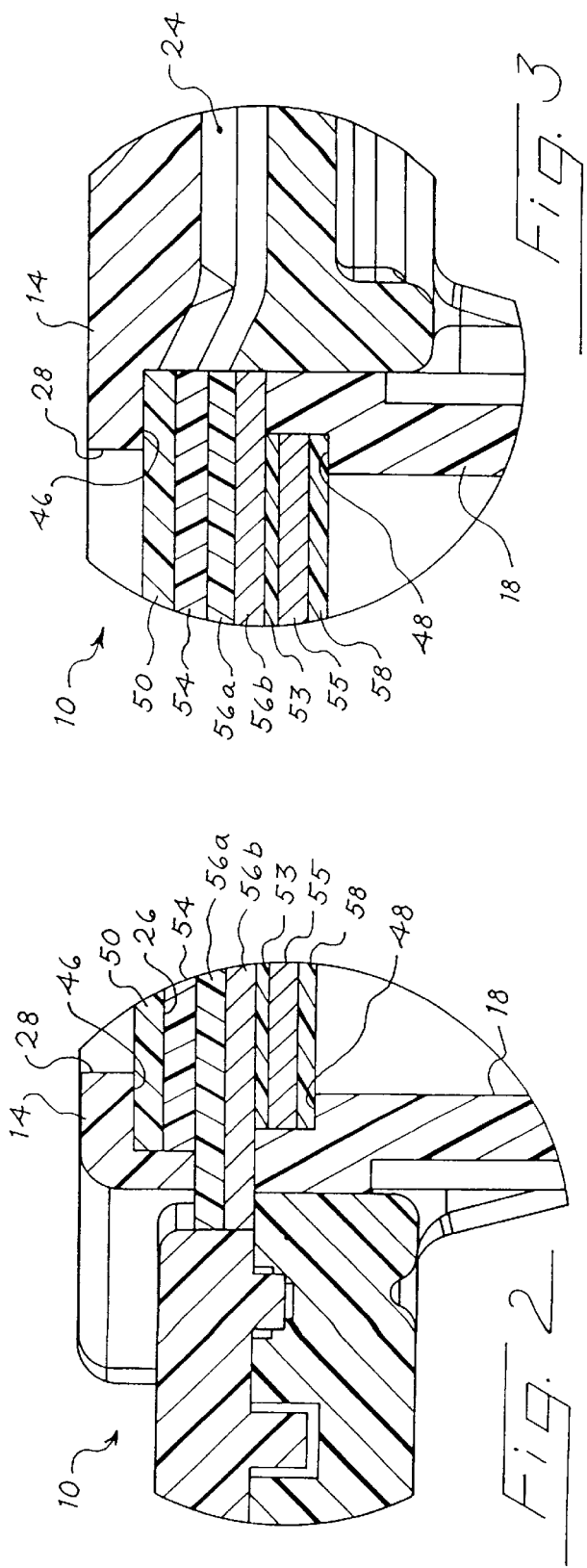

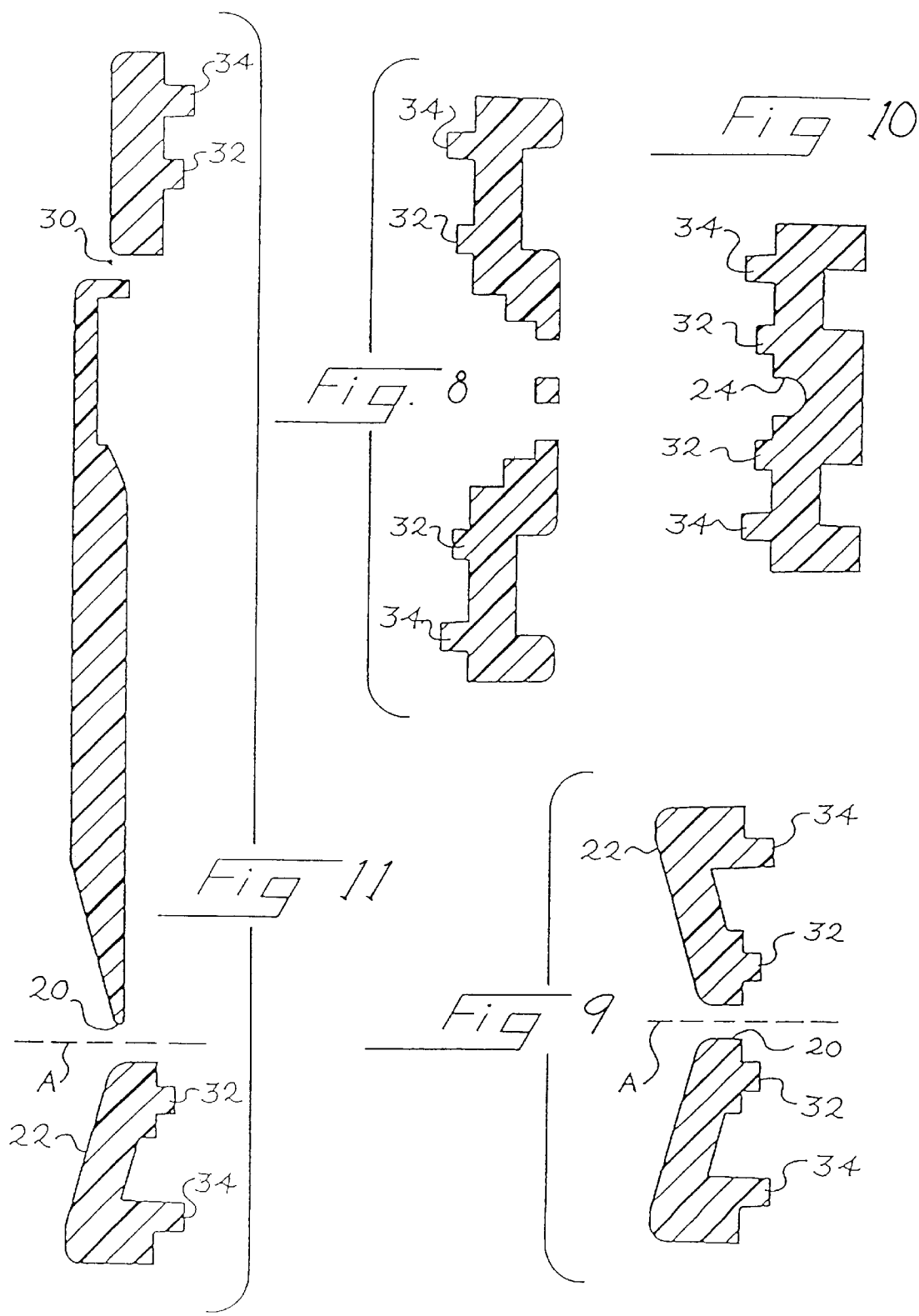

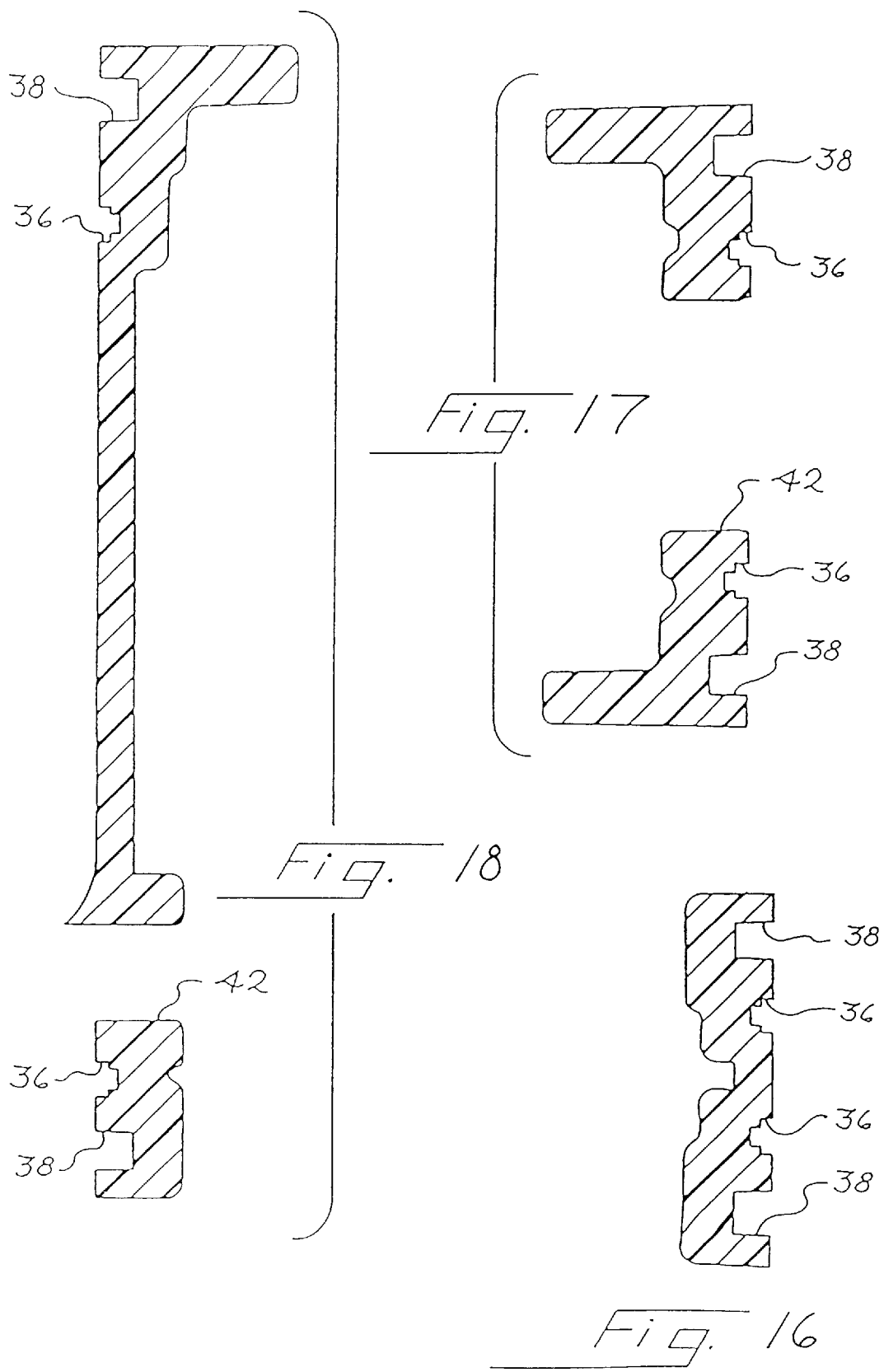

METHOD FOR STABILIZING AMINOTRANSFERASE ACTIVITY IN A BIOLOGICAL FLUID

FIELD OF THE INVENTION

The present invention is directed generally to the field of stabilizing serum or plasma samples. The preferred embodiments include compositions that allow retention of at least 80% of the aminotransferase activities in a serum or plasma sample to be retained 48 hours post collection.

BACKGROUND

Several heart and liver diseases have been correlated with abnormally high levels of serum aspartate aminotransferase (AST). Examples of such conditions include acute myocardial infarction, pulmonary embolism, acute pancreatitis, viral and toxic hepatitis, and acute cirrhosis. Generally speaking, AST is elevated in diseases affecting tissues rich in AST. Similarly, human alanine aminotransferase (ALT) is an enzyme that is leaked into the serum of a patient suffering from hepatic diseases such as viral hepatitis, hepatocirrhosis, etc., and is important as a clinical marker.

Serodiagnosis of ALT and AST is a good indicator of whether a particular subject is undergoing distress in a diseased state. More particularly, the presence of elevated AST or ALT is a good indicator of liver disease. The assays for determining the activity of these enzymes generally involve extracting blood from the subject and immediately employing one of a number of calorimetric or kinetic ultraviolet techniques. Such techniques are described in for example U.S. Pat. Nos. 5,834,226, 5,952,211, and 4,769,323, which describe various assays for aminotransferase activity. A particularly well characterized assay for AST and ALT is that sold by Sigma Chemical Company as part of the aspartate aminotransferase (AST/GOT) test kits.

Regardless of the assay format employed to determine aminotransferase activity, it has been common practice to use these assays on venous blood drawn from the patient in a clinical setting. The assays are performed on serum separated from the whole blood drawn from the patient. This is due to the fact that the aminotransferase activity from red blood cells is sufficiently high to mask the activity present in the serum from other organs. Thus, it is preferable to remove the red blood cells from whole blood in order to obtain an accurate reading of the levels of aminotransferase activity attributable to origins other than the red blood cells.

In addition, aminotransferase enzyme activity in the serum is relatively unstable as a function of time, and, for this reason, it has been common practice to analyze serum relatively quickly once the serum is separated from whole blood. This practice has meant that serodiagnosis for indications of disorders in which the aminotransferase activities are elevated have been performed in the clinical setting as opposed to a setting distant from the hospital.

BRIEF SUMMARY

A need presently exists for a method and system for serodiagnostic purposes, where the sample is stable and retains aminotransferase activity over an extended period of time post collection without the need for additional conditions, such as freeze drying or refrigeration. Such a method would facilitate collection of a sample of blood at a location remote from the location at which analysis is performed. For example, such a method would allow for a patient to collect a sample of blood at home and mail it to diagnostic laboratory for testing.

The preferred method and system described below stabilize blood plasma by separating plasma from whole blood and contacting the plasma with a stabilizing composition. This stabilizing composition is effective to retain an amino transferase activity in the plasma at an activity of at least about 80 percent of initial activity, 48 hours post-collection at a temperature of about 25°C. The presently preferred stabilizing composition comprises between about 20 mM to about 1 M EDTA and between about 1 mM and about 1 M citrate, when the composition is in solution.

The foregoing paragraphs have been provided by way of introduction, and they are not intended to limit the scope of the following claims.

BRIEF DESCRIPTION OF THE DRAWINGS

FIG. 1 is a longitudinal sectional view of a device that may be used in a preferred embodiment of the present invention.

FIGS. 2 and 3 are enlarged sectional views of the indicated portions of FIG. 1.

FIGS. 8, 9, 10, and 11 are cross-sectional views taken along the corresponding section lines of FIGS. 4 and 6.

FIGS. 16, 17, and 18 are cross-sectional views taken along corresponding section lines of FIGS. 12 and 14.

DETAILED DESCRIPTION OF THE PREFERRED EMBODIMENTS

Figure 4:
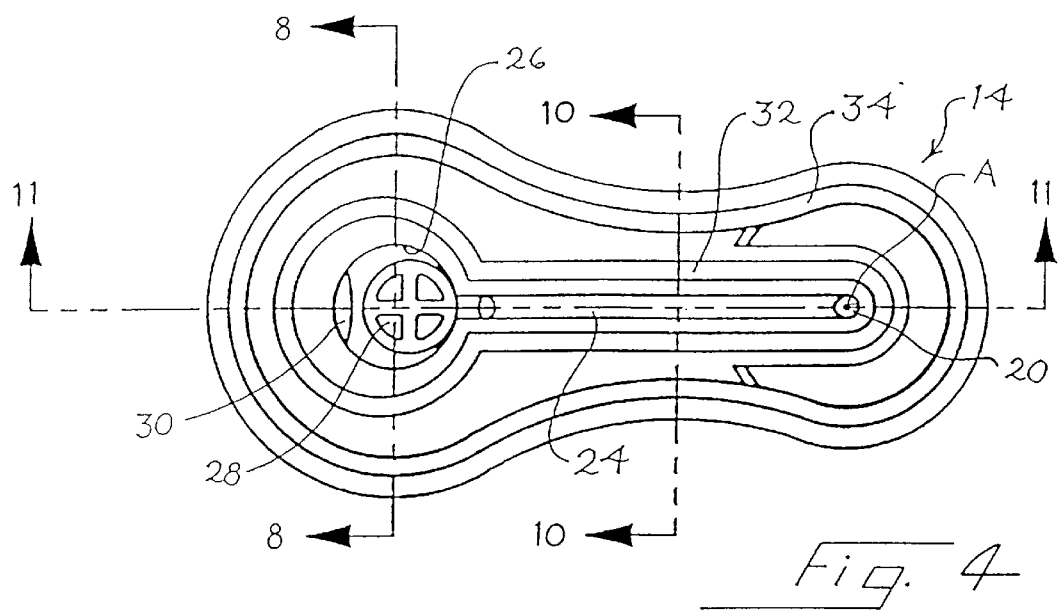
FIGS. 4, 5, 6, and 7 are bottom, side, top and end views, respectively, of the upper part 14 of the device 10 of FIGS. 1 through 3.
Figure 5:
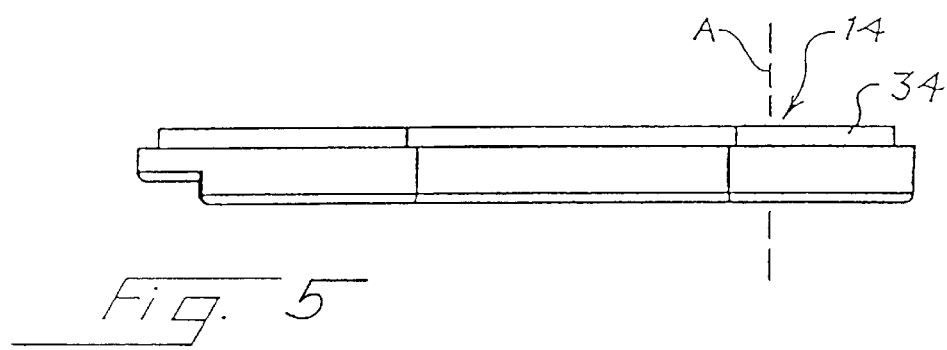
Figures 6, 7:
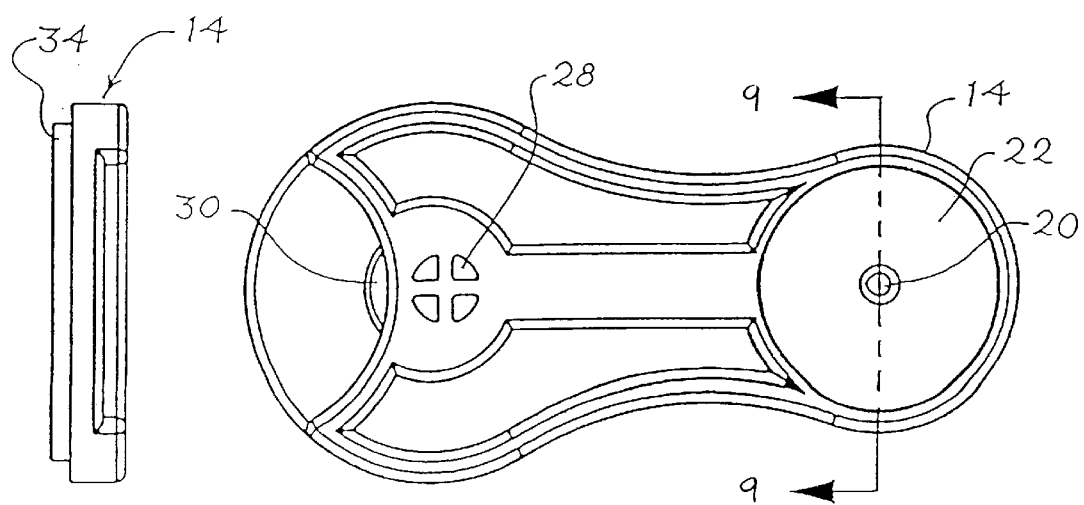
Figure 12:
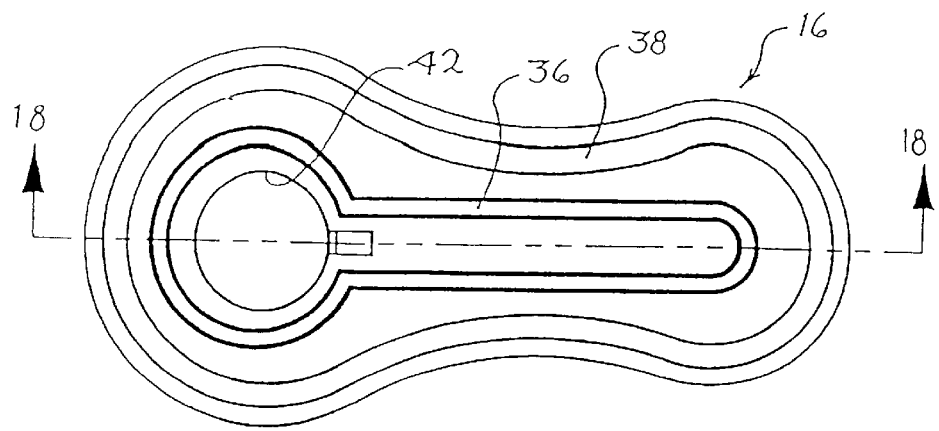
FIGS. 12, 13, 14, and 15, are top, side, bottom, and end views, respectively, of the lower part 16 of the device 10 of FIGS. 1 through 3.
Figure 13:
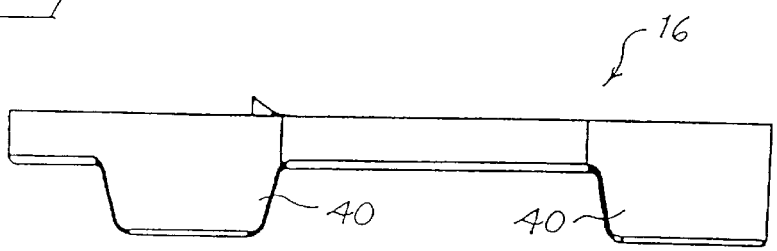
Figures 14, 15:
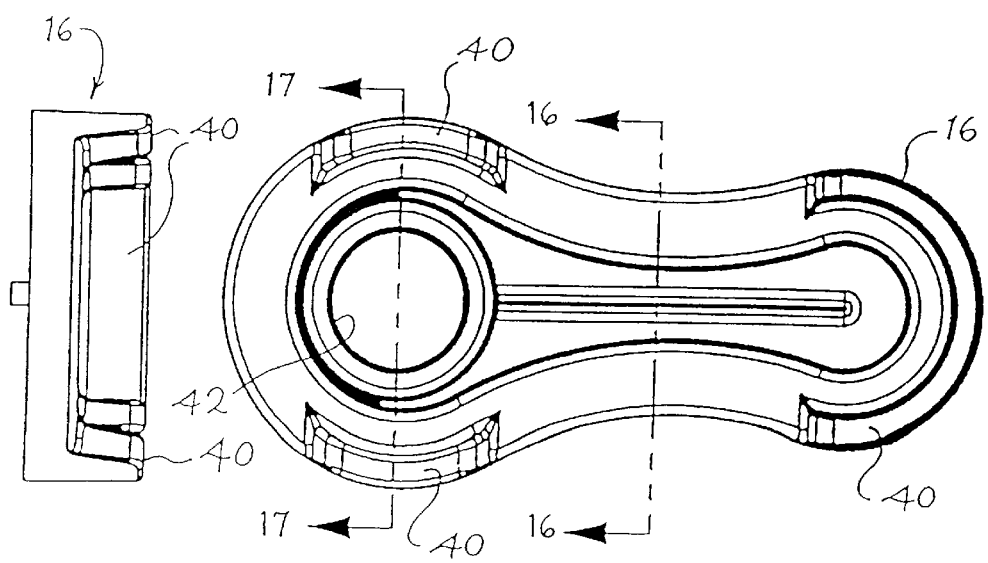

The preferred embodiments described below include methods and compositions for the stabilization of biological fluids in such a manner as to allow retention of an amino transferase activity in plasma at an activity of at least about 80% of initial activity, 48 hours post-collection. More particularly, these embodiments stabilize plasma by bringing it into contact with a stabilization composition which preserves the aminotransferase activity at an activity of at least about 80% of initial activity, 48 hours post-collection. Surprisingly, it has been found that this stabilized activity is maintained even in dried serum or plasma. As such, the methods and compositions described below greatly facilitate collection of serum samples at a location remote from the location of analysis and yet still provide meaningful diagnostic data when the analysis is subsequently performed.

In specific embodiments, the inventor has shown that the presence of ethylenediametetraacetic acid (EDTA) and citrate in a stabilizing composition is effective to retain aminotransferase activities at the desired levels. In addition, there are other components that have a beneficial effect in prolonging the activity of aminotransferase.

As used herein the term "serum" means that portion of whole blood that remains after the suspended materials have been removed. More particularly, serum is the fluid that remains after red blood cells, fibrinogen and fibrin have been removed from whole venous blood. The term "plasma" is used herein to refer to the fluid part of blood as distinguished from the suspended materials. Plasma differs from serum in that plasma contains fibrinogen component that is absent in serum. As used herein, the terms "plasma" and "serum" connote fluids that are substantially free of red blood cells. Plasma and serum may contain some red blood cells, so long as such red blood cells do not interfere substantially with the aminotransferase activity of the plasma or serum.

As described above, it is preferable to remove red blood cells from a sample being assayed for aminotransferase activity. This is because erythrocytes (red blood cells) contain aminotransferases. Erythrocytes act much like an osmometer, swelling and shrinking in response to the changes in osmotic pressure of the surrounding liquid. When blood is placed in an environment that is more hypotonic that the natural environment within the body, red blood cells may swell until they rupture and deposit their contents into the surrounding fluid. For this reason, removal of the red blood cell component of blood from a given sample may improve the accuracy of readings of aminotransferase activity that is present in circulation due to the result of some aberration in liver, heart, pancreatic or other function.

Stabilizing Compositions

The preferred embodiments described below stabilize plasma or serum such that the aminotransferase activity in the plasma or serum is retained to at least about 80% of the initial activity after collection of the plasma or serum. This level of activity is retained at these levels whether the plasma or serum is maintained as a dry sample or as a wet sample.

In addition, in these embodiments, this activity is retained over a broad temperature range of from about −70° C. to about 50° C. As such, the red blood cells may be removed from the whole blood, and the resultant plasma or serum will still retain its activity when stored at any temperature in this range. In preferred embodiments, the plasma is stored at about 25° C. Likewise, the dried sample of these embodiments may be stored at any temperature in the above range and still retain the activity as described.

The plasma or serum may be contacted with the stabilizing solution prior to separation of the plasma or serum from whole blood, during the separation of the plasma or serum from whole blood, after the separation of the plasma or serum from whole blood, or indeed during two or even all three steps.

The stabilizing composition in it simplest form comprises EDTA and citrate. EDTA is a well known buffer constituent that is commonly used as a chelator of divalent cations. Solid EDTA is readily available to those of skill in the art. In addition, a 2% solution of the disodium salt of EDTA is sold as an anticoagulant (catalog no. 285-4. Sigma Chemical Co., St. Louis Mo.). The stabilizing composition preferably provides an amount of EDTA effective to produce a concentration of between about 20 mM to about 1M ethylenediaminetetraacetic acid in the plasma or serum. The concentration is produced when the plasma or serum is contacted with the stabilizing composition. As such, it should be understood that the EDTA may be presented in a dried form or as a solution that will reach the desired concentration upon mixing with the appropriate volume of plasma or other biological fluid.

The range of between about 20 mM to about 1M is an exemplary range. It is envisioned that any concentration between these two concentrations will be useful. Thus the composition may be such that it will yield 20 mM, 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, 525 mM, 550 mM, 575 mM, 600 mM, 625 mM, 650 mM, 675 mM, 700 mM, 725 mM, 750 mM, 775 mM, 800 mM, 825 mM, 850 mM, 875 mM, 900 mM, 925 mM, 950 mM, 975 mM or 1M in a solution in which the plasma or serum sample is presented.

The citrate component of the stabilizing composition also is known as an anticoagulant. Sodium citrate, available from Sigma Chemical Co., may be used in the stabilizing composition in an amount effective to yield a concentration of between about 1 mM and about 1M citrate. As with the EDTA, it should be understood that this citrate may be presented in a dried form or as a solution that will provide the desired concentration upon mixing with the appropriate volume of biological fluid.

The range of between about 1 mM to about 1M citrate is an exemplary range. It is envisioned that any concentration between these two concentrations will be useful. Thus, the composition may be such that it will yield 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, 525 mM, 550 mM, 575 mM, 600 mM, 625 mM, 650 mM, 675 mM, 700 mM, 725 mM, 750 mM, 775 mM, 800 mM, 825 mM, 850 mM, 875 mM, 900 mM, 925 mM, 950 mM, 975 mM or 1M citrate in a solution in which the plasma or other biological fluid is presented. Although preferred embodiments of the present invention employ sodium citrate as part of the stabilizing composition, it is envisioned that any citrate that is known to be useful as part of a buffer or as an anticoagulant solution will be useful herein. As such citrate dextrose, citrate phosphate dextrose and citric acid as well as sodium citrate are specifically contemplated to be useful.

In addition to the EDTA and citrate, it is envisioned that some stabilizing solutions also may contain one or more of other reagents that will also aid in the stabilization of the plasma or other biological fluid. Such reagents include but are not limited to succinate, sucrose and sodium azide. Succinate can be used in a concentration of between about 10 mM to about 1M when the biological fluid is applied to the composition. The succinate may be presented in a dried form or as a solution that will reach the desired concentration upon mixing with the appropriate volume of biological fluid. Again the concentration range of between about 10 mM to about 1M is exemplary and any concentration therebetween may be employed such as 10 mM, 11 mM, 12 mM, 13 mM, 14 mM, 15 mM, 16 mM, 17 mM, 18 mM, 19 mM, 20 mM, 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, 525 mM, 550 mM, 575 mM, 600 mM, 625 mM, 650 mM, 675 mM, 700 mM, 725 mM, 750 mM, 775 mM, 800 mM, 825 mM, 850 mM, 875 mM, 900 mM, 925 mM, 950 mM, 975 mM or 1 M succinate in a solution in which the plasma or other biological fluid is presented.

In certain embodiments, the stabilizing composition contains sufficient sucrose to yield a concentration of between about 1 mM to about 1M sucrose. Similarly to the EDTA above, the sucrose may be present any concentration between this range. Other embodiments comprise sodium azide that forms a concentration of between about 0.01% to about 1% of the final solution of biological fluid being stabilized (weight/volume). Any range between these two figures is also specifically contemplated to be useful in the present invention, thus the stabilized biological fluid may have a final concentration of 0.01%; 0.02%; 0.03%; 0.04%; 0.05%; 0.06%; 0.07%; 0.08%, 0.09%; 0.10%; 0.15%; 0.2%; 0.25%; 0.3%; 0.35%; 0.4%; 0.45%; 0.5%; 0.55%; 0.60%; 0.65%; 0.7%; 0.75%; 0.8%; 0.85%; 0.90%; 0.95% and 1% sodium azide.

By way of example only, the following table provides some exemplary stabilizing solutions. All of these stabilizing solutions have been found to stabilize plasma or serum such that aminotransferase activity is retained to at least about 80% of initial activity for at least 48 hours at 25° C. As above, concentrations are measured in the stabilized biological fluid prior to drying.

TABLE 1

Preferred Stabilizing Solutions

| Solution No. | 1 | 2 | 3 | 4 | 5 | 6 | 7 |
|---|---|---|---|---|---|---|---|
| EDTA | 200 mM | 200 mM | 200 mM | 200 mM | 200 mM | 200 mM | 200 mM |
| Citrate | 50 mM | 50 mM | 50 mM | 50 mM | 50 mM | 250 mM | 250 mM |
| Sucrose | Not added | Not added | 100 mM | 100 mM | 100 mM | 100 mM | 100 mM |
| Succinate | Not added | 50 mM | Not added | 50 mM | 50 mM | 250 mM | 250 mM |
| Sodium Azide | Not added | 0.05% | Not added | Not added | 0.05% | 0.05% | Not added |

In particular embodiments, it was found that with solution 7 there was no loss in activity of aminotransferase activity even one week after collection of the sample and there was only 8.7% loss in activity two weeks after collection when the sample was maintained at room temperature in a dried/undried state. This demonstrates that solution 7 provides a stabilizing effect on serum or plasma such that aminotransferase activity in that sample may be reliably determined some time post collection instead of immediately after collection.

Unless otherwise indicated, the component reagents of the stabilizing composition may be obtained from Sigma Chemical Company (St. Louis, Mo.).

Separating Methods

As mentioned above, it is desirable to remove red blood cells from whole blood in order to yield appropriate measurements of aminotransferase activity in a given blood specimen. Methods for the separation of plasma or serum from whole blood are well known to those of skill in the art. It is envisioned that any such method may be used with the stabilizing compositions described herein.

There are various ways in which the stabilizing compositions may be employed. For example, such compositions may be added as a buffer to the whole blood solution prior to the separation step. In such an embodiment, the composition may be present in the blood collection tubes, e.g. heparinized glass tubes used in blood collection by capillary action.

In another embodiment, the stabilizing composition may be brought into contact with the whole blood during the separation of the red blood cells from the whole blood. In such an embodiment, the composition may be added as a solution or it may be present on the separating platform. The term "separating platform" is used to refer to that portion of the separation device or apparatus that the blood solution passes through as it is being separated into component parts. This platform may be as simple as a piece of filter paper impregnated with the stabilizing composition.

Alternatively, the platform may be a depth filter such as, for example, any of the following filters: AP2504200, AP2003500, AW1904700 (Millipore, Corporation, Bedford, Mass.); the BTS-SP filters available from USF Filtration and Separation (San Diego, Calif.) (described in U.S. Pat. Nos. 4,774,038, 5,171,445, 5,118,734, 5,834,107, and 5,888,059); U.S. Filter/FILTERITE filters available from U.S. Filter (U.S. Filter/Filterite, San Diego, Calif.); HEMASEP V filters and the CYTOSEP solid phase plasma separation system available from Pall Corporation (Port Washington, N.Y.); and Whatman filter products for blood separation such as the GF/AVA, F487-09; F487-14; F147-11; GF/D; F145-02 and GF/DVA (Whatman International Ltd., Kent, England, U.K.)

A variety of blood separation devices and methods are described in, for example, U.S. Pat. Nos. 5,788,942, 5,558,834, 5,939,331, and 4,990,457, each incorporated herein by reference. U.S. Pat. No. 5,788,942 describes an element for the quantitative analysis of an analyte contained in whole blood including a blood filtration layer consisting of a layer of cloth selected from a micro-fibrous cloth made of non-glass fibers having an average fiber diameter of from 0.1 to 10 m, and a detection layer laminated with said blood filtration layer. Plasma is separated from the whole blood through the blood filtration layer while avoiding hemolysis of red blood cells, and the filtered plasma is received by the detection layer. In such a device, it is envisioned that the stabilizing compositions described above may be impregnated into the blood filtration layer to stabilize the plasma separated from the whole blood.

The device described in U.S. Pat. No. 5,939,331 comprises four zones: a sample receiving zone, a labeling zone, a capture zone and an absorbent zone. The sample receiving zone contains an irreversibly immobilized reagent that removes substantially all red blood cells from the whole blood sample. Flow through the device is via capillary migration, and all of the dissolved or dispersed components in the sample flow at substantially equal rates and with relatively unimpaired flow through the device. The stabilizing compositions described above may be placed in the receiving zone.

In U.S. Pat. No. 5,558,834 the device for separating the cellular components of whole blood from plasma or serum and assaying the plasma or serum includes a filter pad that separates the cellular components of whole blood from the serum or plasma, and a test pad that assays the serum or plasma for a predetermined soluble constituent. The filter pad effectively separates and retains cellular components of the whole blood sample, thereby eliminating assay interference by the cellular components of whole blood. The method described in that patent includes the steps of contacting the whole blood with a test device including a filter pad made of a suitable carrier matrix such that the cellular components of the whole blood are separated from the plasma or serum as the blood permeates through the filter pad. The cell-free plasma or serum then saturates a test pad that is in contact with the filter pad. After the plasma or serum saturates the test pad, the test pad is examined for a qualitative or quantitative response to a predetermined soluble constituent of the whole blood. The stabilizing compositions described above can be placed on the filter pad or indeed the test pad to preserve aminotransferase activity that is at least 80% of the initial activity even 48 hour post collection.

It should be understood that the above methods are described merely as illustrations of the blood separation methods that are available to those of skill in the art. In addition to the above methods, there are numerous other for separation methods that will be well known to those of skill in the art and can be employed with the compositions of the present invention.

A particularly preferred method is one which employs a blood separation device described in PCT publication No. WO 99/57559, incorporated herein by reference in its entirety. The device described therein permits collection, drying and transport of a defined quantity of a body fluid such as blood. The device is designed to precisely collect a predefined volume of blood. A blood sample is introduced into a housing via an opening and a channel into an internal compartment that contains an absorbent material and is vented to atmosphere by one or more openings absorbed into a porous element. The blood sample then dries in the housing for subsequent analysis. Such a device may be employed to produce a dried stabilized plasma or serum sample using the compositions of the present invention. Such compositions may be impregnated onto the absorbent material or may be presented to the material in solution such that the material is saturated with the stabilizing composition prior to the contacting of the blood. The presence of the compositions of the present invention will stabilize the plasma or serum component of the blood such that the aminotransferase activity of the sample will be retained at 80% or more of the initial activity 48 hours post separation.

Kits

Materials and reagents for the separation, stabilization and testing of plasma or serum for aminotransferase activity may be assembled together in a kit. When the components of the kit are provided in one or more liquid solutions, the liquid solution preferably is an aqueous solution, with a sterile aqueous solution being particularly preferred. Alternatively, the components of the kit may also be provided in dried or lyophilized forms. In certain embodiments, the compositions of the present invention may be presented on an appropriate platform for the separation of plasma or serum from whole blood as described herein above. When reagents or components are provided as a dried form, the addition of the blood will provide reconstitution of the composition components to the concentrations of the present invention.

The kits of the present invention also may typically include a means for containing the plasma stabilizing compositions in close confinement for commercial sale such as, e.g., injection or blow-molded plastic containers into which the desired blood collection devices are retained. Irrespective of the number or type of containers, the kits of the invention also may comprise, or be packaged with, an instrument for assisting with the collection of blood such as a sterile needle for those embodiments in which merely a drip of blood is needed or a heparinized blood collection tube where a greater amount of blood is required. Such an instrument will, of course, be present in a sterile packaging.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute a preferred mode for its practice. However, those of skill in the art should, in light of the present disclosure, appreciate that many changes can be made in the specific embodiment disclosed and still obtain a like or similar result without departing from the spirit and scope of the invention.

Example 1

Operation of the Serum Separator Device

Figure 19:
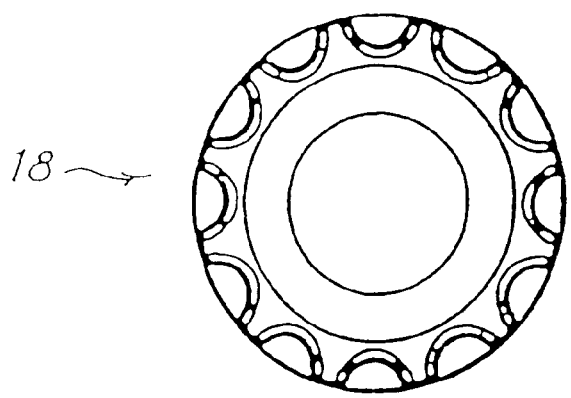
FIGS. 19, 20, and 21 are bottom, side, and top views, respectively, of the plug 18 of the device 10 of FIGS. 1 through 3.
Figure 20:
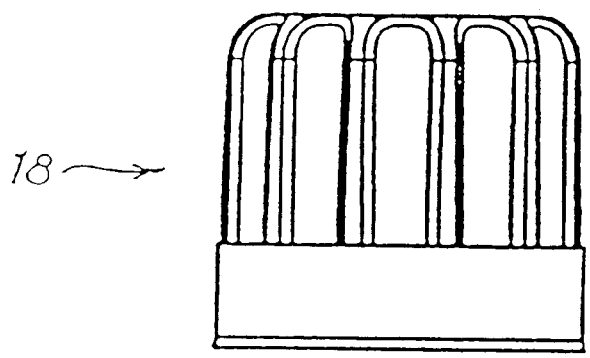
Figure 21:
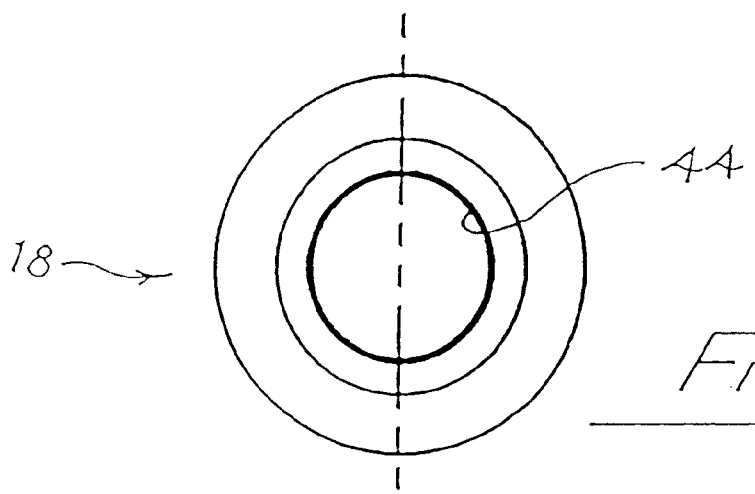

FIGS. 1 through 21 show a device much like that from WO 99/57559 that can be used for collecting and drying a serum or plasma from a blood sample. As shown in FIG. 1, the device 10 includes a housing 12 that is made up of an upper part 14 (FIGS. 4–11), a lower part 16 (FIGS. 12–18), and a plug 18 (FIGS. 19–21).

As best shown in FIG. 1, the upper part 14 defines an external opening 20 centered within a recess 22. The external opening 20 is aligned with an axis A, and the opening 20 provides fluid communication between the exterior of the housing 12 and a channel 24. The channel 24 is oriented substantially transversely to the axis A in this embodiment. In other embodiments, the channel 24 can be oriented at other nonparallel angles with respect to the axis A. The channel 24 provides a fluid flow path from the external opening 20 to an internal compartment 26 that is laterally offset from the external opening 20. The upper part 14 defines first and second openings 28, 30 that are in fluid communication with the internal compartment 26. First and second ribs 32, 34 extend around the internal compartment 26, the channel 24 and the external opening 20.

The lower part 16 defines first and second recesses 36, 38 positioned and sized to receive the first and second ribs 32, 34, respectively. The lower part 16 also defines three legs 40. These legs 40 extend downwardly from the lower surface of the lower part 16 and provide stable support for the device 10. The lower part 16 also defines a cylindrically shaped socket 42 that is in fluid communication with the internal compartment 26.

The plug 18 is sized to fit within the socket 42 in a press fit such that the plug 18 can be inserted into and removed from the housing 12 in a convenient manner. The plug 18 defines a central passageway 44 that is in fluid communication with the internal compartment 26. The plug 18 defines a slightly enlarged distal end and the socket 42 defines a slightly enlarged internal end. These features provide increased retention forces tending to hold the plug 18 in place when the plug 18 is fully inserted into the socket 42. Other retention methods may be used, including for example screw threads, bayonet locks, splines, snap fits, and the like.

As best shown in FIGS. 2–3, various membranes are mounted in the internal compartment 26. The upper part 14 defines a ledge 46 adjacent to the first opening 28, and the plug 18 defines a ledge 48 adjacent to the central passageway 44. The ledges 46, 48 retain the porous sheets described below in position in the internal compartment 26.

In particular, a vapor-permeable, liquid-barrier layer such as a porous hydrophobic membrane 50 can be positioned immediately adjacent to the ledge 46, and a serum collection membrane 58 is positioned immediately adjacent to the ledge 48. The ledges 46, 48 hold the membranes 50, 58 in place during use. The membrane 50 is optional in this embodiment.

In the embodiment of FIGS. 2 and 3, five sheets of porous material are mounted in the internal compartment 26 between the hydrophobic membrane 50 and the serum collection membrane 58. These five sheets include a blood transport membrane 54, two blood separation membranes 56a and 56b, a barrier membrane 53, and a porous membrane 55. The blood transport membrane 54 transports the blood across the entire area of the internal compartment 26, and the blood transport membrane 54 is in fluid communication with the channel 24. The blood separation membranes 56a, 56b operate as a filter that separates blood cells from blood serum. Serum which has passed the blood separation membranes 56a, 56b passes through the barrier membrane 53 and the porous membrane 55 to the serum collection membrane 58.

The serum collection membrane 58 is thus positioned on the opposite side of the blood separation membranes 56a, 56b from the channel 24. The serum collection membrane 58 acts as a test pad that collects the serum sample for analysis. The barrier layer 53 is interposed between the blood separation membrane 56b and the serum collection membrane 58, and the barrier layer 53 serves several purposes:

1. It substantially prevents the re-uptake of serum into the blood separation membranes 56a, 56b during drying of the sample;
2. It prevents hemolysis that occurs in the blood separation membranes 56a, 56b from contaminating the sample in the serum collection membrane 58;
3. It allows excess serum to be retained in this additional layer.

The device 10 is assembled by first placing the hydrophobic membrane 50, the blood transport membrane 54, and the blood separation membranes 56a, 56b in the compartment-defining recess of the upper part 14. Then the lower part 16 is assembled to the upper part 14. As shown in FIGS. 1 and 2, the lower part 16 locks the blood separation membranes 56a, 56b in place, thereby restraining any of the membranes 50, 54, 56a, 56b from moving out of the internal compartment 26 as long as the upper and lower parts 14,16 remain in an assembled condition. The upper and lower parts 14, 16 can be held together by any suitable method, including a mechanical press fit, a mechanical welding or heat sealing operation, or an adhesive bonding operation.

Once the upper and lower parts 14,16 have been assembled as described above, the plug 18 carrying the serum collection membrane 58, the filter layer 55 and the barrier layer 53 is positioned in the socket 42, thereby closing the internal compartment 26 and bringing the barrier layer 53 into contact with the blood separation layer 56b.

In use of the device 10, a drop of blood is introduced into the recess 22. The walls of the channel 24 are preferably formed of a material that facilitates capillary flow, and the channel 24 therefore conducts blood from the external opening 20 to the internal compartment 26, where the blood is introduced onto the blood transport membrane 54. Serum from the blood then passes through the blood separation membranes 56a, 56b (which block the flow of blood cells), and serum is collected on the collection membrane 58. The porous hydrophobic membrane 50 allows vapor to escape from the internal compartment 26 while preventing the movement of blood out of the internal compartment 26. Once the membranes 54, 56a, 56b are saturated with blood, the capillary action ceases and no further blood is transported into the internal compartment 26 by the channel 24. As vapor leaves the internal compartment by the porous hydrophobic membrane 50, the blood sample, including the serum collected on the serum collection membrane 58, dries. The user can see a reddening of the blood separation membrane 56a through the second opening 30 to confirm proper operation of the device 10.

Once the blood sample has dried, the plug 18 can be removed from the socket 42, thereby removing the serum collection membrane 58 from the internal compartment 26 for analysis. The dried serum sample can then be analyzed in any desired manner.

Simply by way of example, the following preferred materials and dimensions can be used. It should be understood that the present invention is not limited to the specific details of construction described below.

By way of example, the internal compartment 26 can define a volume less than 1 ml and the channel 24 can define a cross-sectional dimension of less than 3 mm. The porous element in the embodiment described above substantially fills the entire internal compartment 26. In alternative embodiments, the porous element in a dry state fills at least 20% of the volume of the internal compartment 26. The channel 24 may be left empty of any absorbent material; alternately an absorbent material may be placed in the channel 24.

Table 2 provides examples of materials that can be used for the membranes 50 through 58.

TABLE 2

Preferred Materials

| Reference No. | Preferred Membrane Material |
| --- | --- |
| 50 | Ultra-high-hydrophobic-molecular weight, polyethylene filter with median pore size of 7 microns (e.g. Porex Technologies 7744) |
| 54, 55 | High density polyethylene filter with pore size of 80–120 microns (e.g. Porex Technologies X4588) |
| 56a | Modified polyester plasma separation medium (e.g. Pall Hemasep ® V) |
| 56b | Asymmetric polysulfone membrane (e.g. US filter BTS SP300) |
| 53 | Reinforced mixed cellulose esters barrier membrane (e.g. Millipore SA 1J017H99) |
| 58 | Cotton fiber serum collection membrane (e.g. Schleicher & Schuell S903) |

It should be noted that in the present invention any one or more of these membranes as well as plug 18 may be impregnated or soaked with the stabilizing compositions of the present invention.

Table 3 provides examples of dimensions that can be used for the device 10.

TABLE 3

Preferred Dimensions

| Feature | Dimension (mm unless otherwise indicated) |
| --- | --- |
| Diameter of opening 20 | 1.6 |
| Length of channel 24 | 2.5 |
| Width of channel 24 | 1.6 |
| Height of channel 24 | 1.4 |
| Diameter of membranes 50, 54 | 6.3 |
| Diameter of membranes 56a and 56b | 8.4 |
| Diameter of membranes 53, 55, 58 | 6.3 |
| Distance between ledges 46, 48 | 4.1 |
| Volume of compartment 26 | 124 mm$^3$ |

The upper and lower parts 14, 16 and the plug 18 can be injection molded if desired from many suitable material. As described above, the selected material should provide the capillary action described above that draws blood from the external opening 20 via the channel 24 to the internal compartment 26. The following materials are believed suitable: ABS (e.g. Bayer Lustran ABS 243) or polyethylene (e.g. Phillips Marlex PE HHM 5502 BN).

The membranes 54, 56a, 56b, 53, 55, 58 taken together make up a porous element 60 disposed in the internal compartment 26.

The blood transport membrane, the blood separation membrane 56 and the serum collection membrane 58 are preferably formed of hydrophilic media that can uniformly absorb and distribute the wet blood. The device 10 provides the advantage of collecting a well-controlled volume of blood. This precision of collection allows for more accurate and precise analytical determination of clinical chemistry analytes. In addition the stabilizing compositions of the present invention afford retention of aminotransferase activity in the sample. The dried serum or plasma sample can be kept inside the device at ambient temperatures and sent to a laboratory for testing.

Because the device 10 allows one to easily collect a defined volume of blood in the dried blood sample, even an untrained user can precisely and consistently collect samples for testing that are of optimum quality and quantity for accurate and precise analytical analysis. Another advantage of the device 10 is that once the blood sample is inside the apparatus there is a lowered chance of contamination or loss of integrity of the sample. The housings protect the sample from being contaminated or physically compromised.

As used herein, the term "membrane" is intended broadly to encompass a wide variety of porous materials, including but not limited to membrane filters, depth filters, and various porous sheet materials.

Example 2

Serum Stabilization

The serum was separated from whole blood in a serum separator device comprising a hydrophobic plastic, Porex x4588 (reference 54,58 in the above example); Hemasep® V (reference 56a in the above example); and SA1J017H99 (placed between the membranes 56b and 58) assembled as described in Example 1 above. In certain of the devices, the serum collection membrane was treated with solutions 1–7 described in Table 1.

The whole blood was applied to the device and allowed to separate. The dried serum spots were subsequently left to dry overnight and assayed for AST and ALT activity on the following day. The ALT and AST was determined as a function of time after collection as well as at various storage temperatures.

The AST/GOT assay employed for the determination of aminotransferase activity was obtained from Sigma Chemical Co. The reaction proceeds according to the following scheme:

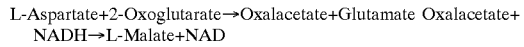

L-Aspartate+2-Oxoglutarate→Oxalacetate+Glutamate Oxalacetate+ NADH→L-Malate+NAD

The rate of decrease of the absorbance at 334, 340 or 365 nm due to the formation of NAD is directly proportional to the rate of oxalacetate formation and hence AST activity. The same assay may be used with L-Alanine which will yield pyruvic acid instead of oxalacetate and the rate of decrease of the absorbance at 334, 340 or 365 nm due to the formation of NAD will be directly proportional to the rate of pyruvate formation.

Alternately, the assay described above may be modified by adding HCl to destroy unreacted NADH, and then adding NaOH to destroy $NAD^+$ and to produce a fluorescent product. The concentration of this fluorescent product is then measured fluorimetrically at 455 nm, using an excitation beam centered at 360 nm.

TABLE 4

The average stability of ALT and AST as a percentage of the initial value when the plasma sample was not treated with a stabilizing solution:

|  | % Recovery −70° C. | % Recovery Room Temp | % Recovery at 37° C. |
|---|---|---|---|
| ALT: 36.3 ± 22.25 | 100 ± 0.00 | 83.35 ± 5.35 | 67.10 ± 2.4 |
| AST: 36.75 ± 21.95 | 100 ± 0.00 | 98.375 ± 5.725 | 95.4 ± 6.3 |

Stabilizing compositions 6 and 7 provided the greatest stability of the ALT and AST activities as indicated in Table 5 and 6. It should be noted that these are exemplary and that the other solutions listed in Table 1 may work to eater or lesser degree in the stabilization of the ALT and AST activities.

TABLE 5

Stabilization of ALT activity with stabilizing solutions 6 and 7 various storage temperatures (−70° C., room temperature, 37° C. and 50° C.) over varying lengths of time (Day 1, Day 4 and Day 7 post storage). Measured Enzyme Activity as a Percentage of Original Value

|  | Solution 6 | | | Solution 7 | | |
|---|---|---|---|---|---|---|
| Enzyme Level | Low (20 Units/L) | Medium (40 Units/L) | High (90 Units/L) | Low (20 Units/L) | Medium (40 Units/L) | High (90 Units/L) |
| Day 1: | | | | | | |
| −70° C. | 100 | 100 | 100 | 100 | 100 | 100 |
| RmT | 93.3 | 105 | 102 | 93.80 | 100 | 95.20 |
| 37° C. | 77 | 89.50 | 107 | 71.90 | 112 | 96.40 |
| 50° C. | 93.3 | 100 | 91.60 | 93.80 | 105 | 106 |
| Day 4: | | | | | | |
| −70° C. | 100 | 100 | 100 | 100 | 100 | 100 |
| RmT | 90.20 | 98.10 | 101.10 | 88 | 104 | 100 |
| 37° C. | 88.00 | 94.40 | 90.50 | 105 | 92.20 | 98.80 |
| 50° C. | 82.90 | 77.80 | 72.60 | 80.50 | 88.20 | 91.80 |
| Day 7: | | | | | | |
| −70° C. | 100 | 100 | 100 | 100 | 100 | 100 |
| RmT | 97.70 | 105.80 | 92.20 | 87.50 | 91.50 | 85.70 |
| 37° C. | 95.50 | 107.80 | 95.50 | 97.90 | 83.10 | 85.70 |
| 50° C. | 100 | 102 | 85.80 | 93.80 | 81.40 | 78.60 |

TABLE 6

Stabilization of AST activity with stabilizing solutions 6 and 7 at various storage temperatures (−70° C., room temperature, 37° C. and 50° C.) over varying lengths of time (Day 1, Day 4 and Day 7 post storage). Measured Enzyme Activity as a Percentage of Original Value

|  | Solution 6 | | | Solution 7 | | |
|---|---|---|---|---|---|---|
| Enzyme Level | Low (20 Units/L) | Medium (40 Units/L) | High (90 Units/L) | Low (20 Units/L) | Medium (40 Units/L) | High (90 Units/L) |
| Day 1: | | | | | | |
| −70° C. | 100 | 100 | 100 | 100 | 100 | 100 |
| RmT | 100 | 100 | 102 | 112 | 100 | 97.90 |
| 37° C. | 78 | 108 | 107 | 78.80 | 112 | 75.50 |
| 50° C. | 90.20 | 128 | 95.70 | 100 | 105 | 67 |
| Day 4: | | | | | | |
| −70° C. | 100 | 100 | 100 | 100 | 100 | 100 |
| RmT | 87.80 | 92.30 | 98.00 | 77 | 104 | 100 |

TABLE 6-continued

Stabilization of AST activity with stabilizing solutions 6 and 7
at various storage temperatures (−70° C., room temperature,
37° C. and 50° C.) over varying lengths of time
(Day 1, Day 4 and Day 7 post storage).
Measured Enzyme Activity as a Percentage of Original Value

| | Solution 6 | | | Solution 7 | | |
|---|---|---|---|---|---|---|
| Enzyme Level | Low (20 Units/L) | Medium (40 Units/L) | High (90 Units/L) | Low (20 Units/L) | Medium (40 Units/L) | High (90 Units/L) |
| 37° C. | 91.80 | 92.30 | 93.10 | 91 | 92.20 | 103 |
| 50° C. | 93.90 | 83.30 | 81.40 | 86.40 | 88.20 | 94.60 |
| Day 7: | | | | | | |
| −70° C. | 100 | 100 | 100 | 100 | 100 | 100 |
| RmT | 102 | 103 | 96.00 | 86.20 | 91.50 | 85.70 |
| 37° C. | 102 | 101.70 | 97.10 | 96.10 | 83.10 | 89.50 |
| 50° C. | 109 | 110 | 94.10 | 86.20 | 81.40 | 94.30 |

These data demonstrate that the serum stabilization compositions of the present invention will be useful in maintaining the aminotransferase activity of a sample to at least about 80% of the initial activity even when stored at temperatures as high as 50° C.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of stabilizing plasma comprising:
   a) separating plasma from whole blood; and
   b) contacting said plasma with a stabilizing composition containing a divalent cation chelating agent and an anticoagulant, wherein said stabilizing composition is present in an amount effective to retain an amino transferase activity in said plasma at an activity level of at least about 80% of initial activity, 48 hours post-collection at a temperature of about 25° C.

2. The method of claim 1, wherein said stabilizing composition together with said plasma comprises about 20 mM to about 1M ethylenediaminetetraacetic acid (EDTA) and about 1 mM to about 1M citrate.

3. The method of claim 1, wherein said plasma is contacted with said composition prior to separation from whole blood.

4. The method of claim 1, wherein said plasma is contacted with said composition after separation from whole blood.

5. The method of claim 1, wherein said plasma is contacted with said composition during separation from whole blood.

6. The method of claim 1, further comprising drying said plasma.

7. The method of claim 1, further comprising separating serum from said plasma.

8. The method of claim 1, wherein, said stabilizing composition together with said plasma further includes about 10 mM to about 1M succinate.

9. The method of claim 1, wherein said stabilizing composition together with said plasma further includes about 1 mM to about 1M sucrose.

10. The method of claim 1, wherein said stabilizing composition together with said plasma further includes about 0.01% to about 1% sodium azide (weight/volume).

11. The method of claim 1, wherein said stabilizing composition causes said enzyme activity to be retained at a storage temperature of between about −70° C. to about 45° C.

12. The method of claim 11, wherein said stabilizing composition causes said enzyme activity to be retained at a storage temperature of between about 2° C. to about 28° C.

13. The method of claim 1, wherein said enzyme activity is an indicator of liver disease.

14. The method of claim 1, wherein said enzyme activity is the activity of an enzyme selected from the group consisting of aspartate transaminase (AST) and alanine transaminase (ALT).

15. The method of claim 1, wherein said separating comprises removing red blood cells from said whole blood.

16. The method of claim 15, wherein said separating comprises retaining red blood cells with a depth filter.

17. The method of claim 16, wherein said depth filter comprises a density filter.

18. The method of claim 17, wherein said depth filter comprises a plurality of density filters arranged in series with increasing density.

19. The method of claim 17, wherein said stabilizing composition is impregnated onto said filter to yield appropriate component concentrations upon contact with said whole blood.

20. The method of claim 15, further comprising depositing said plasma produced from said removal of red blood cells from said whole blood on a transport medium selected from the group consisting of a high density polyethylene filter having a pure size of 80 to 120 microns and a cotton fiber serum collection membrane.

21. The method of claim 20, further comprising drying said plasma to yield dried stabilized plasma on said transport medium.

22. The method of claim 21, wherein said transport medium comprises said stabilizing composition.

23. The method of claim 22, wherein said dried plasma retains at least 80% of the initial enzyme activity when re-hydrated.

24. A method of stabilizing a biological fluid containing an aminotransferase enzyme comprising contacting said biological fluid with a composition comprising between about 20 mM to about 1M EDTA and about 1 mM to about 1 M citrate, when said composition is in solution with said biological fluid, wherein said amino transferase enzyme retains at least 80% of its initial activity 48 hours after collection of said biological fluid.

25. The method of claim 24, further comprising drying said biological fluid on a transport medium.

26. The method of claim 24, wherein said biological fluid comprises plasma.

27. The method of claim 24, wherein said biological fluid comprises serum.

28. The method of claim 24, wherein said aminotransferase comprises a liver-derived aminotransferase.

29. The method of claim 28, wherein said aminotransferase is selected from the group consisting of alanine transaminase and aspartate transaminase.

* * * * *